US012800570B2

(12) United States Patent
Ng et al.

(10) Patent No.: US 12,800,570 B2
(45) Date of Patent: Nov. 17, 2026

(54) ASSAY FOR MEASURING POTENCY OF GENE THERAPY DRUG PRODUCT

(71) Applicant: Prevail Therapeutics, Inc., New York, NY (US)

(72) Inventors: Mary Ng, Brooklyn, NY (US); Timothy Fenn, Greenwich, CT (US); Patricia Biezonski, Valley Stream, NY (US); Jorge Haller, Tarrytown, NY (US); Yong Dai, Northborough, MA (US)

(73) Assignee: PREVAIL THERAPEUTICS, INC.

( * ) Notice: Subject to any disclaimer, the term of this patent is extended or adjusted under 35 U.S.C. 154(b) by 844 days.

(21) Appl. No.: 18/031,494

(22) PCT Filed: Oct. 15, 2021

(86) PCT No.: PCT/US2021/055200
§ 371 (c)(1),
(2) Date: Apr. 12, 2023

(87) PCT Pub. No.: WO2022/081985
PCT Pub. Date: Apr. 21, 2022

(65) Prior Publication Data

US 2024/0044869 A1 Feb. 8, 2024

Related U.S. Application Data

(60) Provisional application No. 63/092,189, filed on Oct. 15, 2020.

(51) Int. Cl.

| | |
|---|---|
| ***G01N 33/50*** | (2006.01) |
| ***C12N 9/24*** | (2006.01) |
| ***C12N 15/86*** | (2006.01) |
| ***C12Q 1/34*** | (2006.01) |
| ***G01N 33/58*** | (2006.01) |

(52) U.S. Cl.
CPC ....... *G01N 33/5008* (2013.01); *C12N 9/2402* (2013.01); *C12N 15/86* (2013.01); *C12Q 1/34* (2013.01); *G01N 33/582* (2013.01); *C12N 2750/14141* (2013.01); *C12Y 302/01045* (2013.01)

(58) Field of Classification Search
CPC .......... C12N 15/86; C12N 2750/14141; C12Y 302/01045; C12Q 1/34; G01N 33/5008
See application file for complete search history.

(56) References Cited

U.S. PATENT DOCUMENTS

| | | | |
|---|---|---|---|
| 10,837,028 | B2 | 11/2020 | Abeliovich et al. |
| 11,060,113 | B2 | 7/2021 | Abeliovich et al. |
| 2020/0231954 | A1 | 7/2020 | Abeliovich et al. |
| 2020/0338148 | A1 | 10/2020 | Abeliovich et al. |
| 2021/0332385 | A1 | 10/2021 | Abeliovich et al. |
| 2022/0119843 | A1 | 4/2022 | Dai et al. |

FOREIGN PATENT DOCUMENTS

| | | | |
|---|---|---|---|
| WO | WO-2016100556 | A1 | 6/2016 |
| WO | WO-2019070891 | A1 | 4/2019 |
| WO | WO-2019070893 | A1 | 4/2019 |
| WO | WO-2019070894 | A1 | 4/2019 |
| WO | WO-2019084068 | A1 | 5/2019 |
| WO | WO-2022035903 | A2 | 2/2022 |

OTHER PUBLICATIONS

Deen, M. C., et al., 2020, Selective Fluorogenic β-Glucocerebrosidase Substrates for Convenient Analysis of Enzyme Activity in Cell and Tissue Homogenates, ACS Chem. Biol. 15:824-829.*
Berrin, J.-G., et al., 2003, Substrate (aglycone) specificity of human cytosolic β-glucosidase, Biochem. J. 373:41-48.*
Korschen, H. G., et al., Feb. 2013, The Non-lysosomal Beta-Glucosidase GBA2 Is a Non-integral Membrane-associated Protein at the Endoplasmic Reticulum (ER) and Golgi, J. Biol. Chem. 288(5):3381-3393.*
Haller, J.F., et al., "Endogenous β-glucocerebrosidase activity in Abca12$^{-/-}$epidermis elevates ceramide levels after topical lipid application but does not restore barrier function," Journal of Lipid Research, Mar. 2014, 55(3):493-503.
International Search Report and Written Opinion for International Application No. PCT/US2021/055200 dated Mar. 2, 2022, 12 pages.
Morabito, G., et al., "AAV-PHP.B-Mediated Global-Scale Expression in the Mouse Nervous System Enables GBA1 Gene Therapy for Wide Protection from Synucleinopathy," Molecular Therapy, Dec. 6, 2017, 25(12):2727-2742.
Rowland, R.J., et al., "A baculoviral system for the production of human β-glucocerebrosidase enables atomic resolution analysis," Acta Crystallographica, Jun. 2020, 76(pt 6):565-580.

* cited by examiner

*Primary Examiner* — Jeffrey S Parkin
(74) *Attorney, Agent, or Firm* — Brian C. Cholewa

(57) ABSTRACT

Disclosed herein is a cell-based assay for determining potency of a recombinant viral vector expressing a transgene.

26 Claims, 2 Drawing Sheets

Specification includes a Sequence Listing.

| | Replicates 1-4 | | | | Replicates 1-4 | | | | Replicates 1-4 | | | |
|---|---|---|---|---|---|---|---|---|---|---|---|---|
| | 1 | 2 | 3 | 4 | 5 | 6 | 7 | 8 | 9 | 10 | 11 | 12 |
| A | RS dilution 1 | RS dilution 1 | RS dilution 1 | RS dilution 1 | TS 1 dilution 1 | TS 1 dilution 1 | TS 1 dilution 1 | TS 1 dilution 1 | TS 2 dilution 1 | TS 2 dilution 1 | TS 2 dilution 1 | TS 2 dilution 1 |
| B | RS dilution 2 | RS dilution 2 | RS dilution 2 | RS dilution 2 | TS 1 dilution 2 | TS 1 dilution 2 | TS 1 dilution 2 | TS 1 dilution 2 | TS 2 dilution 2 | TS 2 dilution 2 | TS 2 dilution 2 | TS 2 dilution 2 |
| C | RS dilution 3 | RS dilution 3 | RS dilution 3 | RS dilution 3 | TS 1 dilution 3 | TS 1 dilution 3 | TS 1 dilution 3 | TS 1 dilution 3 | TS 2 dilution 3 | TS 2 dilution 3 | TS 2 dilution 3 | TS 2 dilution 3 |
| D | RS dilution 4 | RS dilution 4 | RS dilution 4 | RS dilution 4 | TS 1 dilution 4 | TS 1 dilution 4 | TS 1 dilution 4 | TS 1 dilution 4 | TS 2 dilution 4 | TS 2 dilution 4 | TS 2 dilution 4 | TS 2 dilution 4 |
| E | RS dilution 5 | RS dilution 5 | RS dilution 5 | RS dilution 5 | TS 1 dilution 5 | TS 1 dilution 5 | TS 1 dilution 5 | TS 1 dilution 5 | TS 2 dilution 5 | TS 2 dilution 5 | TS 2 dilution 5 | TS 2 dilution 5 |
| F | RS dilution 6 | RS dilution 6 | RS dilution 6 | RS dilution 6 | TS 1 dilution 6 | TS 1 dilution 6 | TS 1 dilution 6 | TS 1 dilution 6 | TS 2 dilution 6 | TS 2 dilution 6 | TS 2 dilution 6 | TS 2 dilution 6 |
| G | FB | FB | FB | FB | FB | FB | FB | FB | FB | FB | FB | FB |
| H | Blank | Blank | Blank | Blank | Blank | Blank | Blank | Blank | Blank | Blank | Blank | Blank |

FIG. 1

| ID | Relative Potency |
|---|---|
| Sample 1 | <0.37 |
| Sample 2 | 2.53 |
| Sample 3 | 0.74 |
| Sample 4 | 3.96 |
| Sample 5 | 1.00 |

SEQUENCE LISTING

<160> NUMBER OF SEQ ID NOS: 3

<210> SEQ ID NO 1
<211> LENGTH: 536
<212> TYPE: PRT
<213> ORGANISM: Homo sapiens

<400> SEQUENCE: 1

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365
```

```
Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535
```

<210> SEQ ID NO 2
<211> LENGTH: 1608
<212> TYPE: DNA
<213> ORGANISM: Artificial Sequence
<220> FEATURE:
<223> OTHER INFORMATION: Codon-optimized Glucocerebrosidase

<400> SEQUENCE: 2

```
atggaattca gcagccccag cagagaggaa tgccccaagc ctctgagccg ggtgtcaatc     60

atggccggat ctctgacagg actgctgctg cttcaggccg tgtcttgggc ttctggcgct    120

agaccttgca tccccaagag cttcggctac agcagcgtcg tgtgcgtgtg caatgccacc    180

tactgcgaca gcttcgaccc tcctaccttt cctgctctgg gcaccttcag cagatacgag    240

agcaccagat ccggcagacg gatggaactg agcatgggac ccatccaggc caatcacaca    300

ggcactggcc tgctgctgac actgcagcct gagcagaaat tccagaaagt gaaaggcttc    360

ggcggagcca tgacagatgc cgccgctctg aatatcctgg ctctgtctcc accagctcag    420

aacctgctgc tcaagagcta cttcagcgag gaaggcatcg gctacaacat catcagagtg    480

cccatggcca gctgcgactt cagcatcagg acctacacct acgccgacac acccgacgat    540

ttccagctgc acaacttcag cctgcctgaa gaggacacca agctgaagat ccctctgatc    600

cacagagccc tgcagctggc acaaagaccc gtgtcactgc tggcctctcc atggacatct    660

cccacctggc tgaaaacaaa tggcgccgtg aatggcaagg gcagcctgaa aggccaacct    720

ggcgacatct accaccagac ctgggccaga tacttcgtga agttcctgga cgcctatgcc    780

gagcacaagc tgcagttttg ggccgtgaca gccgagaacg aaccttctgc tggactgctg    840

agcggctacc cctttcagtg cctgggcttt acacccgagc accagcggga ctttatcgcc    900

cgtgatctgg gacccacact ggccaatagc acccaccata atgtgcggct gctgatgctg    960

gacgaccaga gactgcttct gccccactgg gctaaagtgg tgctgacaga tcctgaggcc   1020

gccaaatacg tgcacggaat cgccgtgcac tggtatctgg actttctggc ccctgccaag   1080
```

-continued

```
gccacactgg gagagacaca cagactgttc cccaacacca tgctgttcgc cagcgaagcc   1140

tgtgtgggca gcaagttttg ggaacagagc gtgcggctcg gcagctggga tagaggcatg   1200

cagtacagcc acagcatcat caccaacctg ctgtaccacg tcgtcggctg gaccgactgg   1260

aatctggccc tgaatcctga aggcggccct aactgggtcc gaaacttcgt ggacagcccc   1320

atcatcgtgg acatcaccaa ggacaccttc tacaagcagc ccatgttcta ccacctggga   1380

cacttcagca agttcatccc cgagggctct cagcgcgttg gactggtggc ttcccagaag   1440

aacgatctgg acgccgtggc tctgatgcac cctgatggat ctgctgtggt ggtggtcctg   1500

aaccgcagca gcaaagatgt gcccctgacc atcaaggatc ccgccgtggg attcctggaa   1560

acaatcagcc ctggctactc catccacacc tacctgtggc gtagacag                1608


<210> SEQ ID NO 3
<211> LENGTH: 145
<212> TYPE: DNA
<213> ORGANISM: Dependoparvovirus Adeno-associated virus 2

<400> SEQUENCE: 3

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145
```

ASSAY FOR MEASURING POTENCY OF GENE THERAPY DRUG PRODUCT

CROSS-REFERENCE TO RELATED APPLICATIONS

This application is a U.S. National Stage Application under 35 U.S.C. § 371 of International Patent Application No. PCT/US2021/055200, filed on Oct. 15, 2021, which claims the benefit of U.S. Provisional Patent Application No. 63/092,189, filed on Oct. 15, 2020, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL_017_01WO_SeqList_ST25.txt, date recorded: Oct. 15, 2021, file size ~7,474 bytes).

TECHNICAL FIELD

The disclosure relates generally to the field of gene therapy. More specifically, the disclosure provides a cell-based assay for analyzing potency of compositions comprising a recombinant viral vector expressing a transgene.

BACKGROUND

Recombinant viral vectors encoding glucocerebrosidase (GCase; encoded by the GBA1 gene) are useful for treating disorders such as Parkinson's disease and Gaucher disease. There is a need for an assay to measure relative potency of recombinant viral compositions delivering GCase that are intended to be used for gene therapy.

SUMMARY

Provided herein is a method for measuring the relative potency of a test sample comprising a first recombinant virus comprising a transgene encoding glucocerebrosidase (GCase), the method comprising: a) transducing a first plurality of cells with the test sample; b) incubating the transduced first plurality of cells under conditions sufficient to express GCase; c) harvesting a first cell lysate from the transduced first plurality of cells; d) combining the first cell lysate with resorufin-beta-D-glucopyranoside; e) imaging the first cell lysate to obtain a first fluorescence reading; f) transducing a second plurality of cells with a reference standard comprising a second recombinant virus comprising a transgene encoding GCase; g) incubating the transduced second plurality of cells under conditions sufficient to express GCase; h) harvesting a second cell lysate from the transduced second plurality of cells; i) combining the second cell lysate with resorufin-beta-D-glucopyranoside; j) imaging the second cell lysate to obtain a second fluorescence reading; and k) comparing the first fluorescence reading with the second fluorescence reading using parallel line analysis to calculate the relative potency of the test sample.

In some embodiments of the methods disclosed herein, the first recombinant virus and the second recombinant virus comprise identical transgenes encoding GCase.

In some embodiments of the methods disclosed herein, the first recombinant virus and/or the second recombinant virus is a recombinant adeno-associated virus (rAAV). In some embodiments, the rAAV comprises an AAV9 capsid protein. In some embodiments, the rAAV comprises an AAV1, AAV2, AAV3, AAV4, AAV5, AAV6, AAV7, AAV8, AAV9, AAV10 or AAV11 capsid protein, or a variant of any of these capsid proteins.

In some embodiments of the methods disclosed herein, the GCase comprises SEQ ID NO:1. In some embodiments, the transgene encoding GCase comprises a codon-optimized nucleotide sequence. In some embodiments, the codon-optimized nucleotide sequence comprises SEQ ID NO: 2.

In some embodiments of the methods disclosed herein, the first plurality of cells and/or the second plurality of cells are HEK-293T or HEK-293 cells.

In some embodiments of the methods disclosed herein, about 1.25 mM resorufin-beta-D-glucopyranoside is combined with the first cell lysate and/or the second cell lysate.

In some embodiments of the methods disclosed herein, the first plurality of cells and the second plurality of cells are seeded in a multi-well plate. In some embodiments, the first plurality of cells and/or the second plurality of cells are seeded at about 20,000 cells per well.

In some embodiments of the methods disclosed herein, the test sample and/or the reference standard are serially diluted before transduction.

In some embodiments of the methods disclosed herein, the first plurality of cells and the second plurality of cells are incubated from about 68 hours to about 81 hours before cell lysate harvesting. In some embodiments, the first plurality of cells and the second plurality of cells are incubated from about 66 hours to about 78 hours after transduction and before cell lysate harvesting.

In some embodiments of the methods disclosed herein, the first plurality of cells is transduced by the test sample at at least two different multiplicities of infection (MOI) of the first recombinant virus. In some embodiments, the second plurality of cells is transduced by the reference standard at at least two different multiplicities of infection (MOI) of the second recombinant virus.

In some embodiments of the methods disclosed herein, the first fluorescence reading and/or the second fluorescence reading reflect a measurement of GCase activity. In some embodiments, the measurement of GCase activity is in relative fluorescence units (RFU)/hour.

In some embodiments of the methods disclosed herein, the comparing step (k) comprises performing a log transformation of the recombinant virus amount and RFU/hour and plotting a standard curve of the log of recombinant virus amount versus the log of RFU/hour for each of the test sample and the reference standard. In some embodiments, the comparing step (k) comprises calculating a linear regression of the log of recombinant virus amount versus the log of RFU/hour for each of the test sample and the reference standard, thereby deriving a test sample slope and a reference standard slope. In some embodiments, the comparing step (k) comprises calculating a linear regression with a common slope using the linear regressions obtained for each of the test sample and the reference standard. In some embodiments, the relative potency is calculated using the formula: Relative potency (%)=$10^{((b-b_{reference})/A)}\times 100$. In some embodiments, the ratio of the slope of the test sample to the common slope is from about 0.60 to about 1.40. In some embodiments, the ratio of the slope of the reference standard to the common slope is from about 0.60 to about 1.40.

In some embodiments, a method disclosed herein further comprises calculating an $R^2$ value for the linear regression of the test sample and the reference standard. In some embodiments, the $R^2$ value for the test sample and the reference standard is greater than or equal to 0.9.

BRIEF DESCRIPTION OF THE DRAWINGS

FIG. 1 is a diagram of a PCR plate map for a rAAV potency assay. "RS" refers to "reference standard". "TS" refers to "test sample".

DETAILED DESCRIPTION

Figure 2:
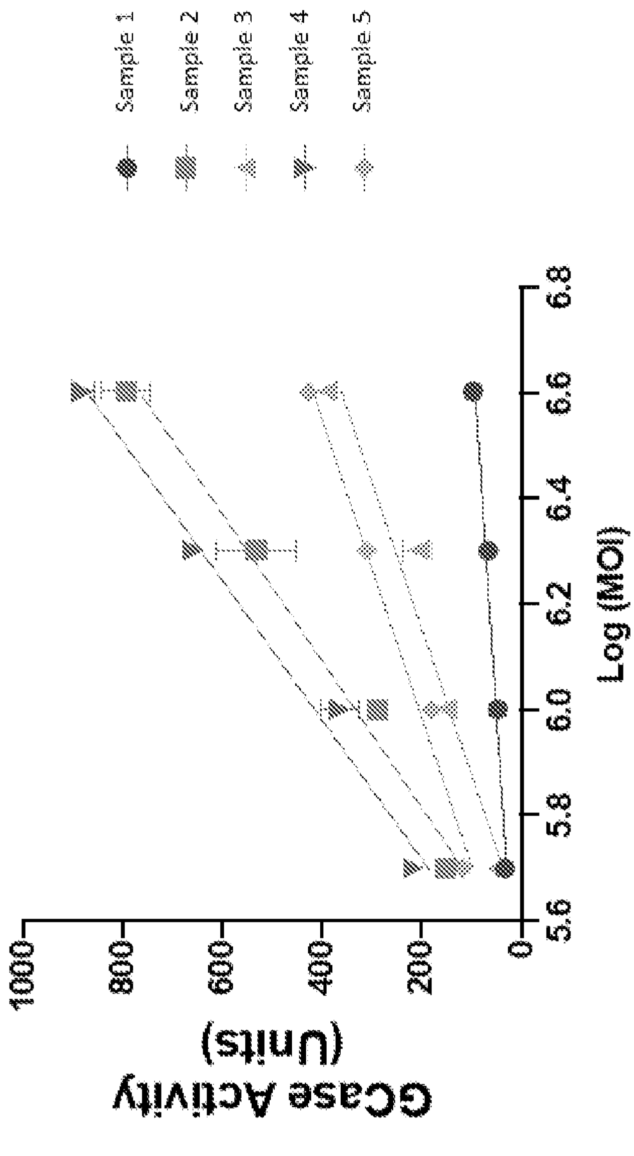
FIG. 2 depicts a line graph and calculations of relative potency of several rAAV samples expressing GCase.

The disclosure relates to cell-based transduction assays to measure relative potency of recombinant viral compositions delivering a transgene encoding glucocerebrosidase (e.g., human glucocerebrosidase). Glucocerebrosidase (also referred to as beta-glucocerebrosidase, lysosomal acid β-glucocerebrosidase, GCase and GBA) is encoded by the GBA1 gene. Subjects with mutations in only one allele of GBA1 are at highly increased risk of Parkinson's disease. Subjects with mutations in both copies of GBA1 suffer from Gaucher disease. Viral compositions delivering a transgene encoding GCase are useful for gene therapy for Parkinson's disease (e.g., Parkinson's disease with a GBA1 mutation) and Gaucher disease.

In some embodiments, a recombinant viral vector encoding GCase is a recombinant adeno-associated virus (rAAV) vector.

The methods disclosed herein utilize the fluorogenic substrate resorufin-β-D-glucopyranoside which, in the presence of GCase, is catalyzed to form the fluorescent product resorufin. Resorufin production is monitored directly as the reaction proceeds to calculate the rate of product formation. In the presence of an excess of resorufin-β-D-glucopyranoside substrate and under the assayed conditions the rate of product formation is linearly proportional to the amount of GCase protein.

The term "recombinant virus" refers to a virus that has been genetically altered, e.g., by the addition or insertion of a heterologous nucleic acid construct into the viral particle.

The term "heterologous" is used herein interchangeably with the term "exogenous", and refers to a substance coming from some source other than its native source. For example, the term "exogenous protein" or "exogenous gene" refers to a protein or gene from a non-AAV source that has been artificially introduced into an AAV genome or AAV particle.

The term "recombinant adeno-associated virus" or "rAAV" refers to a AAV particle or AAV virion comprising a rAAV vector encapsidated by one or more AAV capsid proteins.

The term "rAAV vector" refers to nucleic acids, either single-stranded or double-stranded, having an AAV 5' inverted terminal repeat (ITR) sequence and an AAV 3' ITR flanking a protein-coding sequence operably linked to transcription regulatory elements that are heterologous to the AAV viral genome, for example, one or more promoters and/or enhancers and, optionally, a polyadenylation sequence and/or one or more introns inserted between exons of the protein-coding sequence.

The term "IU" refers to infectious units.

The term "TCID50" refers to the 50% cell culture infectious dose.

The term "USP" refers to the United States Pharmacopeia.

The term "test sample" refers to a sample comprising a rAAV vector comprising a sequence encoding an exogenous protein of interest (e.g., GCase) whose potency is unknown and will be determined using the methods described herein.

The term "reference standard" refers to a composition comprising a rAAV vector encoding an exogenous protein of interest (e.g., GCase) whose potency is known.

In some aspects, provided herein is a method for measuring the relative potency of a test sample comprising a first recombinant virus comprising a transgene encoding glucocerebrosidase (GCase), the method comprising: a) transducing a first plurality of cells with the test sample; b) incubating the transduced first plurality of cells under conditions sufficient to express GCase; c) harvesting a first cell lysate from the transduced first plurality of cells; d) combining the first cell lysate with resorufin-beta-D-glucopyranoside; e) imaging the first cell lysate to obtain a first fluorescence reading; f) transducing a second plurality of cells with a reference standard comprising a second recombinant virus comprising a transgene encoding GCase: g) incubating the transduced second plurality of cells under conditions sufficient to express GCase; h) harvesting a second cell lysate from the transduced second plurality of cells; i) combining the second cell lysate with resorufin-beta-D-glucopyranoside; j) imaging the second cell lysate to obtain a second fluorescence reading; and k) comparing the first fluorescence reading with the second fluorescence reading using parallel line analysis to calculate the relative potency of the test sample.

In some embodiments, the first recombinant virus and the second recombinant virus are identical. In some embodiments, the first recombinant virus and the second recombinant virus are not identical. In some embodiments, the first recombinant virus and the second recombinant virus comprise identical transgenes encoding GCase but are from different manufacturing lots or production lots. In some embodiments, the GCase comprises the amino acid sequence of SEQ ID NO: 1.

In some embodiments, the first plurality of cells and/or the second plurality of cells are HEK-293T or HEK-293 cells.

Methods disclosed herein may be performed in multi-well plates. In some embodiments, a method disclosed herein is performed in a 96-well plate. In some embodiments, the first plurality of cells and the second plurality of cells are seeded in a multi-well plate. In some embodiments, the first plurality of cells and/or the second plurality of cells are seeded at about 20,000 cells per well before transduction with the test sample and the reference standard, respectively. In some embodiments, the cells are allowed to attach overnight at 37° C. and 5% $CO_2$.

In some embodiments, the transduction takes place about 24 hours after cells are seeded.

In some embodiments, the test sample and/or the reference standard are serially diluted before transduction. In some embodiments, the test sample is diluted to 50%, 100%, and 200% of the reference standard. In some embodiments, the serial dilutions produce the following total vector genome (vg) amounts per well: 5.00E+10 vg/well, 3.33E+10 vg/well, 2.22E+10 vg/well, 1.48E+10 vg/well, 9.88E+9 vg/well, and 6.58E+9 vg/well.

In some embodiments, a standard curve of purified recombinant GCase (rGBA, 0 to 333 ng/ml, R&D cat #7410-GHB-020, >95% purity) is run in parallel to the test sample.

In some embodiments, the first plurality of cells is transduced by the test sample at at least two different multiplicities of infection (MOI) of the first recombinant virus. In some embodiments, the second plurality of cells is transduced by the reference standard at at least two different MOIs of the second recombinant virus.

In some embodiments, the first plurality of cells and the second plurality of cells are incubated from about 68 hours to about 81 hours after transduction and before cell lysate harvesting. In some embodiments, the first plurality of cells and the second plurality of cells are incubated from about 2 to about 2.5 hours before a recovery medium (e.g., 10% FBS/DMEM/1 μM Hoechst 33342) is added to the cells. In some embodiments, the first plurality of cells and the second plurality of cells are incubated about 72 hours±6 hours (e.g., from about 66 hours to about 78 hours) after transduction and before cell lysate harvesting. In some embodiments, the incubation takes place at 37° C. and 5% $CO_2$.

In some embodiments, about 1.25 mM resorufin-beta-D-glucopyranoside is combined with the first cell lysate in the combining step (d) and/or the second cell lysate in the combining step (i).

In some embodiments, the imaging step (e) and/or (j) is performed with a plate reader.

In some embodiments, the first fluorescence reading and/or the second fluorescence reading reflect a measurement of GCase activity. In some embodiments, the measurement of GCase activity is in relative fluorescence units (RFU)/hour.

In some embodiments, the comparing step (k) comprises performing a log transformation of the recombinant virus amount and RFU/hour and plotting a standard curve of the log of recombinant virus amount versus the log of RFU/hour for each of the test sample and the reference standard. In some embodiments, the comparing step (k) comprises calculating a linear regression of the log of recombinant virus amount versus the log of RFU/hour for each of the test sample and the reference standard, thereby deriving a test sample slope and a reference standard slope. In some embodiments, the comparing step (k) comprises calculating a linear regression with a common slope using the linear regressions obtained for each of the test sample and the reference standard. In some embodiments, the relative potency of the test sample is calculated using the formula: Relative potency (%)=10^((b−$b_{reference}$)/A)×100. In some embodiments, the ratio of the slope of the test sample to the common slope is from about 0.60 to about 1.40. In some embodiments, the ratio of the slope of the reference standard to the common slope is from about 0.60 to about 1.40.

In some embodiments, the method for measuring the relative potency of a test sample further comprises calculating an $R^2$ value for the linear regression of the test sample and the reference standard. In some embodiments, the $R^2$ value for the test sample and the reference standard is greater than or equal to 0.9. In some embodiments, the $R^2$ value for the test sample and the reference standard is greater than or equal to 0.96.

In some embodiments, the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard. In some embodiments, the relative potency of the viral vector is at least 90% relative to a reference standard.

The infectious titer (also referred to as functional titer) of rAAV vectors is the concentration of viral particles that can infect cells. In some embodiments, cell transduction assays are used for determining infectious titer. In some embodiments, the infectious titer of the viral vector is determined using the method provided in Example 1. In some embodiments, the infectious titer of a composition disclosed herein is from about 8.0E+9 μU/mL to about 1.2E+10 IU/mL. In some embodiments, the infectious titer of a composition disclosed herein is about 8.0E+9 IU/mL, about 8.15E+9 IU/mL, about 8.5E+9 IU/mL, about 9.0E+9 μU/mL, about 9.5E+9 IU/mL, about 9.99E+9 IU/mL, about 1E+10 IU/mL, about 1.12E+10 IU/mL or about 1.2E+10 IU/mL. In some embodiments, the TCID50 of a composition disclosed herein is from about 4,500 vg/IU to about 10,000 vg/IU. In some embodiments, the TCID50 of a composition disclosed herein is about 4,500 vg/IU, about 5,000 vg/IU, about 5,500 vg/IU, about 6,000 vg/IU, about 6,290 vg/IU, about 6,500 vg/IU, about 7,000 vg/IU, about 7,500 vg/IU, about 8,000 vg/IU, about 8,500 vg/IU, about 9,000 vg/IU, about 9,500 vg/IU, about 9,980 vg/IU or about 10,000 vg/IU.

Examples of suitable rAAV vectors that can be used in the methods disclosed herein are disclosed in WO2019/070891, WO2019/070893, WO2019/070894, and WO2019/084068, the disclosure of each of which is incorporated by reference herein in its entirety.

In some embodiments of the methods disclosed herein, a rAAV vector further comprises one or more of the following: a chicken beta actin (CBA) promoter; a cytomegalovirus (CMV) enhancer; a Woodchuck Hepatitis Virus Posttranscriptional Regulatory Element (WPRE); a Bovine Growth Hormone polyA signal tail; an artificial intron; an artificial exon; and one or more of the following transcriptional regulatory activation sites in a promoter region: TATA, RBS, and YY1 (Francois et al., (2005) *J. Virol.* 79(17):11082-11094). The TATA, RBS and YY1 transcriptional regulatory activation sites may be located at the 5' end of the promoter region.

In some embodiments of the methods disclosed herein, a rAAV vector comprises a first AAV inverted terminal repeat (ITR) and a second ITR flanking the polynucleotide encoding a gene product of interest and the related regulatory sequences. In some embodiments, each ITR is a wild-type AAV2 ITR (SEQ ID NO: 3). In some embodiments, each ITR is derived from a wild-type AAV2 ITR.

In some embodiments of the methods disclosed herein, a rAAV vector comprises, in sequential order, a first AAV inverted terminal repeat (ITR), a cytomegalovirus (CMV) enhancer, a chicken beta actin (CBA) promoter, the polynucleotide encoding a human GCase protein, a Woodchuck Hepatitis Virus Posttranscriptional Regulatory Element (WPRE), a Bovine Growth Hormone polyA signal tail and a second AAV ITR. In some embodiments, the polynucleotide encoding a human GCase protein is codon optimized (e.g., codon optimized for expression in human cells). In some embodiments, the polynucleotide encoding a human GCase protein comprises SEQ ID NO: 2. In some embodiments, a rAAV particle comprising a rAAV vector comprising a polynucleotide comprising SEQ ID NO: 2 is referred to as "PR001".

In some embodiments of the methods disclosed herein, a rAAV vector is a self-complementary recombinant adeno-associated virus (scAAV) vector. scAAV vectors are described in, for example, McCarty et al., *Gene Ther.* 2001; 8(16):1248-54.

In some embodiments of the methods disclosed herein, the recombinant virus is AAV. In some embodiments of the methods disclosed herein, a rAAV comprises an AAV9 capsid protein. In some embodiments of the methods disclosed herein, a rAAV comprises an AAV1, AAV2, AAV3, AAV4, AAV5, AAV6, AAV7, AAV8, AAV9, AAV10 or AAV11 capsid protein, or a variant of any of these capsid proteins.

All publications, patents and patent applications are herein incorporated by reference in their entirety to the same extent as if each individual publication, patent or patent application was specifically and individually indicated to be incorporated by reference in its entirety The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention.

EXAMPLE

Example 1: In Vitro Enzymatic Potency Assay for rAAV Encoding Glucocerebrosidase The purpose of this assay is to measure in vitro relative potency of an AAV (e.g. AAV9) encapsulated vector encoding glucocerebrosidase (GCase; encoded by the GBA1 gene) using a cell-based assay.

Laboratory Test Method

The purpose of this method is to measure a dose response of an AAV encapsulated vector encoding glucocerebrosidase (GCase; encoded by the GBA1 gene) in vitro using a cell-based functional assay. This test method may be used for research purposes, such as comparing the responses of different AAV gene therapy product lots.

TABLE 1

| Definitions | |
|---|---|
| AAV9 | Adeno-associated virus serotype-9 |
| CV | Coefficient of variation |
| Excipient | Formulation Buffer |
| FBS | Fetal Bovine Serum |
| FB | Formulation Buffer; same as Excipient |
| GCase | Glucocerebrosidase, also known as β-Glucocerebrosidase |
| Glc | Glucose or glucopyranoside |
| HEK-293T | Human embryonic kidney cells, (contains SV40 T-antigen) |
| PBS | Phosphate-Buffered Saline |
| RT | Room temperature |
| SDS | Safety Data Sheet |
| TS | Test Sample, namely the DS, DP or sample virus |
| VG, vg | Viral Genomes, viral genomes |
| RP | Relative Potency |
| RS | Reference Standard |

TABLE 2

Materials and Equipment

| Material Description | Manufacturer | Item Number |
|---|---|---|
| HEK293T cells | Source: Prevail | N/A |
| DMEM | Gibco | 11-995-065 |
| FBS (heat inactivated) | Gibco | 1008247 |
| Penicillin (10,000 unit/ml) and Streptomycin (10,000 μg/ml) | Gibco | 15140122 |
| TrypLE Select Enzyme (1X) | Gibco | 12563-011 |
| Assay Buffer: 50 mM citric acid, 176 mM K2HPO4, 10 mM sodium taurocholate, and 0.01% Tween-20 at pH 5.9 | Source: Prevail | N/A |
| Poly-D-Lysine 96-well Black/Clear Flat bottom TC-treated microplate | Corning | 356640 |
| Trypan blue stain | Invitrogen | T10282 |
| Hoechst 33342 Stain (16.234 mM) | Molecular probes | H3570 |
| AAVs to be tested | Source: Prevail | N/A |
| Excipient | To match AAV | N/A |
| Dilution plate: 96-well PCR microplate | Axygen | PCR-96-FS-C |
| Protease inhibitors, EDTA free | Pierce | A32955 or A32965 |
| 96-well black plate with clear flat bottom | Corning | 3904 |
| Varioskan Lux Reader | Thermo Fisher Scientific | FA-0049 |
| Biopur Safe Lock 1.5 mL sterile microcentrifuge tubes | Fisher Scientific | 21-402-903 |
| Hemacytometer; INCYTO; disposable; C-chip | Incyte | 22600100 |
| 25 mL sterile disposable reservoirs | Fisher Scientific | 21-381-27C |
| Resorufin-b-D-glucopyranoside | Marker Gene Technologies | M0569 |
| Dimethyl Sulfoxide (DMSO) | Sigma-Aldrich | D2438-50ML |

Background/Theory of Method: PR001 is an exemplary rAAV expressing GBA1. A transduction assay introduces PR001 to the HEK293T cells and results in GCase enzyme expression. Enzyme activity derived from the transduction was assayed in cell lysate using the fluorogenic substrate 4-methylumbelliferyl-β-D-glucopyranoside, which generates the fluorescent product resorufin by GCase catalysis. Relative potency between two or more rAAVs was calculated from the enzymatic activity resulting from the transduction at different amounts of PR001 using parallel line analysis.

TABLE 3

| Reagents/Diluent/Media ITEM |
|---|
| 10% FBS/DMEM/Pen/Strep [Cell Culture Medium] |
| 2% FBS/DMEM |
| 10% FBS/DMEM/1 μM Hoechst 33342 [Recovery Medium] |
| 50 mM Citrate-176 mM Phosphate Assay Buffer, pH 5.9 |
| 2 μM Hoechst 33342 in 2% FBS/DMEM [Transduction Medium] |
| Assay Lysis Buffer with Protease Inhibitor Cocktail Mini Tablet |
| Resorufin-β-D-glucopyranoside [Stock] |

Procedure: HEK293T cells were plated at 20,000 cells/well in a 96-well plate and allowed to attach overnight at 37° C. and 5% C02. Serial dilutions of the AAV were prepared in its excipient as shown in Table 4.

TABLE 4

| Dilution | vg/μL | Volume virus (μL) | Source (dilution) | Volume Excipient (μL) | Volume remaining (μL) |
|---|---|---|---|---|---|
| 1 | 5.00E+09 | 60 | N/A | N/A | 20 |
| 2 | 3.33E+09 | 40 | 1 | 20 | 20 |
| 3 | 2.22E+09 | 40 | 2 | 20 | 20 |
| 4 | 1.48E+09 | 40 | 3 | 20 | 20 |
| 5 | 9.88E+08 | 40 | 4 | 20 | 20 |
| 6 | 6.58E+08 | 40 | 5 | 20 | 20 |

10 μl of AAV dilutions or vehicle were transferred to wells following the plate map in FIG. 1. The resulting total vg were achieved (Table 5).

TABLE 5

| vg/μL | μL added | total vg/well |
|---|---|---|
| 5.00E+09 | 10 | 5.00E+10 |
| 3.33E+09 | 10 | 3.33E+10 |
| 2.22E+09 | 10 | 2.22E+10 |
| 1.48E+09 | 10 | 1.48E+10 |
| 9.88E+08 | 10 | 9.88E+09 |
| 6.58E+08 | 10 | 6.58E+09 |

Cells were incubated for 2 to 2.5 hrs. in a 37° C., 5% $CO_2$ incubator. After incubation, 100 μl of Recovery Medium was added to the cells/transduction medium to the wells for a total volume of 150 μL. Cells were incubated for 72+6 hours at 37° C. and 5% $CO_2$ to allow virally-derived GCase expression.

Cell lysates were harvested. GCase activity was measured by adding 10 μl of 1.25 mM Resorufin-β-D glucopyranoside working solution to black plate with clear flat bottom followed by 40 μL of cell lysate. The plate was immediately read on a Varioskan plate reader at 37° C.

Analysis: A parallel analysis of the data to calculate the relative potency was performed as follows:

1. Calculate the % CV for each vg/well point, it should be ≤30%. Up to one replicate per vg/well point can be discarded to achieve this if necessary.
2. Perform a log transformation of the virus amounts and GCase activity (relative fluorescence units (RFU)/hr).
3. Plot response as Log (RFU/hr) vs Log (virus).
4. Perform a linear regression for each sample.
5. Perform a new linear regression with a common slope "A" (Y=A X+b).
6. Using the parameters obtained in step 5, calculate the relative potency using the following formula:

$$\text{Relative potency (\%)}=10^{\wedge}((b-b\text{reference})/A)\times 100$$

7. Report results relative to reference standard as percentage, no decimals (e.g., if result is 100.50 will be 101%).

TABLE 6

| Assay System Suitability and Sample Criteria | |
|---|---|
| Parameter | Acceptance Criteria |
| Slope to average slope ratio | The ratio of the slope of Analysis step 3 to common slope (Analysis step 4) should be between 0.60-1.40 |
| $R^2$ | The target $R^2$ of linear regression in Analysis step 3 for RS should be >0.9 |
| Reference Standard and test sample replicates | % CV ≤ 30. One replicate can be masked to achieve % CV ≤ 30. |

Test Method Qualification Protocol

Objective: The purpose of this qualification plan is to define the test method to measure relative potency of PR001 in vitro using a cell-based assay. This protocol will demonstrate that the method produces reliable data and is fit for analysis of AAV samples for research and process development purposes (non-GXP).

TABLE 7

| Qualification materials | |
|---|---|
| Material Description | Physical Titer |
| PR001 reference standard | 2.62E+13 vg/mL |
| Specificity control (PR006 product) | 1.64E+13 vg/mL |

Qualification plan: The validation will be performed according to the validation of analytical test methods, a procedure described in the International Conference on Harmonization (ICH) Q2 (R), USP<1032> and USP<1033>. Validation testing will consist of testing AAV9-GBA DP at 50%, 100%, and 200% relative potency levels as well as specificity. To evaluate method linearity, accuracy and precision (repeatability and intermediate precision), each level will be tested by two analysts. Relative potency from each assay is independent and regarded as a single assay determination. Each plate will contain one reference standard and up to two test samples. If system suitability fails on a plate, then the plate will be repeated. If system suitability fails for a sample, then only the failed sample will be repeated. All samples should meet the assay acceptance criteria defined in the method and the validation criteria defined in this protocol. Determination of specificity will also be performed using an unrelated AAV product that does not carry GBAL. Detection and quantitation limits have not been included because they are not relevant to a method that reports relative potency as explained in USP<1032>. Table 8 summarizes the validation procedures and the acceptance criteria that will be used to assess the performance of the method.

TABLE 8

| Summary of Validation Procedure and Qualification Acceptance Criteria | | | |
|---|---|---|---|
| Parameter | Definition | Procedure and Data Analysis | Acceptance Criteria |
| Linearity | The method's ability (within a given range) to obtain test results which are directly proportional to concentration (amount) of analyte in samples. | AAV9-GBA test samples will be diluted to 50%, 100%, and 200% of the reference standard, and will be tested in up to 4 times per concentration. The mean (measured) relative potency will be plotted versus the expected relative potency and analyzed using linear regression. | The coefficient of determination ($R^2$) for linear regression will be ≥0.9. |
| Accuracy | The closeness of agreement between a value accepted as the sample's true value and the value obtained from the measurement. | The linearity data will be evaluated to assess accuracy. The mean % recovery will be calculated at each level. | The mean % recovery at each level will be between 50% and 150% of the theoretical value. |
| Repeatability | The precision (i.e. the closeness of agreement between a series of measurements obtained from multiple sampling of the same homogeneous sample under the prescribed conditions) measured under the same operating conditions over a short interval of time. | The linearity data will be evaluated to assess repeatability. The percent relative standard deviation (% RSD) will be calculated at each level for each assay (i.e. same analyst and same week). | The % RSD will be ≤30% at each level for each analyst for each week. |
| Intermediate Precision | The precision (i.e. the closeness of agreement between a series of measurements obtained from multiple sampling of the same homogeneous sample under the prescribed conditions) expressing variation from different weeks and different analysts. | The linearity data will be evaluated to assess intermediate precision. The overall % RSD will be calculated at each level. | The overall % RSD will be ≤30% at each level. |
| Range | The interval between the upper and lower concentration demonstrating a suitable level of linearity, accuracy and precision. | The results from the linearity, accuracy and precision will be used to determine the method range. | The range will be determined in the study. Sample concentrations within the range must meet the acceptance criteria for linearity, accuracy and precision. |
| Specificity | The ability to unequivocally assess the analyte in the presence of components which may be expected to be present. | The alternate molecule will be tested in one assay by one analyst. | The alternate molecule will not meet the sample acceptance criteria. |

Linearity: AAV9-GBA test samples will be diluted to 50%, 100%, and 200% of the reference standard, and will be tested in seven assays by two analysts. The mean (measured) relative potency will be plotted versus the expected relative potency and analyzed using linear regression. The resulting linearity equation and coefficient of determination ($R^2$) will be reported. Assay plates that fail system suitability not be used for analysis.

Accuracy: The linearity data will be evaluated to assess accuracy. The mean % recovery will be calculated at each level using the following formula:

$$\%\ \text{Recovery} = \left(\frac{\text{Mean Measured Value}}{\text{Theoretical Value}}\right) \times 100\%$$

The % recovery values at each level will be reported.

Repeatability: The linearity data will be evaluated to assess repeatability. The percent relative standard deviation (% RSD) will be calculated at each level for each assay (i.e. same analyst and same week) and reported.

Intermediate Precision: The linearity data will be evaluated to assess repeatability. The overall % RSD will be calculated at each level and reported.

Range: The lowest and highest potency tested that meet the criteria for linearity, accuracy and precision experiments will be used to determine the method range and will be reported.

Specificity: An alternate molecule (specificity sample) will be tested in one assay by one analyst. The specificity sample will be diluted into the assay as if they were AAV9-GBA test samples. The specificity sample is an alternate molecule (AM): PR006.

Data Handling and Reporting: Raw data will be acquired by the SkanIt RE 5.0 software and parallel line analysis will be performed as indicated in the test method above. This data will be exported into a spreadsheet for calculating additional assay parameters (e.g., accuracy and precision). All resulting data, including details of the experiments such as materials, reagents, equipment used and test conditions, will be recorded and reviewed by a second analyst.

Based on the results from all the valid assay runs and all valid concentrations of the reference standard virus and research virus, the overall average relative potency across all runs from the qualification will be used to establish the nominal RP value for these samples for use in further assay executions.

An example of the potency assay data from several PR001 samples is shown in FIG. 2.

TABLE 9

| Sequence Table | |
|---|---|
| GCase amino acid sequence | MEFSSPSREECPKPLSRVSIMAGSLTGLLLLQAVSWASGARPCIPKSFGYSSVVCVCN<br>ATYCDSFDPPTFPALGTFSRYESTRSGRRMELSMGPIQANHTGTGLLLTLQPEQKFQK<br>VKGFGGAMTDAAALNILALSPPAQNLLLKSYFSEEGIGYNIIRVPMASCDFSIRTYTY<br>ADTPDDFQLHNFSLPEEDTKLKIPLIHRALQLAQRPVSLLASPWTSPTWLKTNGAVNG<br>KGSLKGQPGDIYHQTWARYFVKFLDAYAEHKLQFWAVTAENEPSAGLLSGYPFQCLGF<br>TPEHQRDFIARDLGPTLANSTHHNVRLLMLDDQRLLLPHWAKVVLTDPEAAKYVHGIA<br>VHWYLDFLAPAKATLGETHRLFPNTMLFASEACVGSKFWEQSVRLGSWDRGMQYSHSI<br>ITNLLYHVVGWTDWNLALNPEGGPNWVRNFVDSPIIVDITKDTFYKQPMFYHLGHFSK<br>FIPEGSQRVGLVASQKNDLDAVALMHPDGSAVVVVLNRSSKDVPLTIKDPAVGFLETI<br>SPGYSIHTYLWRRQ<br>(SEQ ID NO: 1) |
| Codon-optimized nucleotide sequence encoding GCase | atggaattcagcagccccagcagagaggaatgccccaagcctctgagccgggtgtcaa<br>tcatggccggatctctgacaggactgctgctgcttcaggccgtgtcttgggcttctgg<br>cgctagaccttgcatccccaagagcttcggctacagcagcgtcgtgtgcgtgtgcaat<br>gccacctactgcgacagcttcgaccctcctacctttcctgctctgggcaccttcagca<br>gatacgagagcaccagatccggcagacggatggaactgagcatgggacccatccaggc<br>caatcacacaggcactggcctgctgctgacactgcagcctgagcagaaattccagaaa<br>gtgaaaggcttcggcggagccatgacagatgccgccgctctgaatatcctggctctgt<br>ctccaccagctcagaacctgctgctcaagagctacttcagcgaggaaggcatcggcta<br>caacatcatcagagtgcccatggccagctgcgacttcagcatcaggacctacacctac<br>gccgacacacccgacgatttccagctgcacaacttcagcctgcctgaagaggacacca<br>agctgaagatccctctgatccacagagccctgcagctggcacaaagacccgtgtcact<br>gctggcctctccatggacatctcccacctggctgaaaacaaatggcgccgtgaatggc<br>aagggcagcctgaaaggccaacctggcgacatctaccaccagacctgggccagatact<br>tcgtgaagttcctggacgcctatgccgagcacaagctgcagttttgggccgtgacagc<br>cgagaacgaaccttctgctggactgctgagcggctacccctttcagtgcctgggcttt<br>acacccgagcaccagcgggactttatcgcccgtgatctgggacccacactggccaata<br>gcacccaccataatgtgcggctgctgatgctggacgaccagagactgcttctgcccca<br>ctgggctaaagtggtgctgacagatcctgaggccgccaaatacgtgcacggaatcgcc<br>gtgcactggtatctggactttctggcccctgccaaggccacactgggagagacacaca<br>gactgttccccaacaccatgctgttcgccagcgaagcctgtgtgggcagcaagttttg<br>ggaacagagcgtgcggctcggcagctgggatagaggcatgcagtacagccacagcatc<br>atcaccaacctgctgtaccacgtcgtcggctggaccgactggaatctggccctgaatc<br>ctgaaggcggccctaactgggtccgaaacttcgtggacagccccatcatcgtggacat<br>caccaaggacaccttctacaagcagcccatgttctaccacctgggacacttcagcaag<br>ttcatccccgagggctctcagcgcgttggactggtggcttcccagaagaacgatctgg<br>acgccgtggctctgatgcaccctgatggatctgctgtggtggtggtcctgaaccgcag<br>cagcaaagatgtgcccctgaccatcaaggatcccgccgtgggattcctggaaacaatc<br>agccctggctactccatccacacctacctgtggcgtagacag<br>(SEQ ID NO: 2) |
| Wild-type AAV2 ITR | aggaacccctagtgatggagttggccactccctctctgcgcgctcgctcgctcactga<br>ggccgggcgaccaaaggtcgcccgacgcccgggctttgcccgggcggcctcagtgagc<br>gagcgagcgcgcagagagggagtggccaa<br>(SEQ ID NO: 3) |

NUMBERED EMBODIMENTS

Notwithstanding the appended claims, the disclosure sets forth the following numbered embodiments:

1. A method for measuring the relative potency of a test sample comprising a first recombinant virus comprising a transgene encoding glucocerebrosidase (GCase), the method comprising:
   a) transducing a first plurality of cells with the test sample;
   b) incubating the transduced first plurality of cells under conditions sufficient to express GCase;
   c) harvesting a first cell lysate from the transduced first plurality of cells;
   d) combining the first cell lysate with resorufin-beta-D-glucopyranoside;
   e) imaging the first cell lysate to obtain a first fluorescence reading;
   f) transducing a second plurality of cells with a reference standard comprising a second recombinant virus comprising a transgene encoding GCase;
   g) incubating the transduced second plurality of cells under conditions sufficient to express GCase;
   h) harvesting a second cell lysate from the transduced second plurality of cells;
   i) combining the second cell lysate with resorufin-beta-D-glucopyranoside;
   j) imaging the second cell lysate to obtain a second fluorescence reading; and
   k) comparing the first fluorescence reading with the second fluorescence reading using parallel line analysis to calculate the relative potency of the test sample.
2. The method of embodiment 1, wherein the first recombinant virus and the second recombinant virus comprise identical transgenes encoding GCase.
3. The method of embodiment 1 or 2, wherein the first recombinant virus and/or the second recombinant virus is a recombinant adeno-associated virus (rAAV).
4. The method of embodiment 3, wherein the rAAV comprises an AAV9 capsid protein.
5. The method of embodiment 3, wherein the rAAV comprises an AAV1, AAV2, AAV3, AAV4, AAV5, AAV6, AAV7, AAV8, AAV9, AAV10 or AAV11 capsid protein, or a variant of any of these capsid proteins.
6. The method of any one of embodiments 1-5, wherein the GCase comprises SEQ ID NO:1.
7. The method of any one of embodiments 1-6, wherein the transgene encoding GCase comprises a codon-optimized nucleotide sequence.
8. The method of embodiment 7, wherein the codon-optimized nucleotide sequence comprises SEQ ID NO: 2.
9. The method of any one of embodiments 1-8, wherein the first plurality of cells and/or the second plurality of cells are HEK-293T or HEK-293 cells.
10. The method of any one of embodiments 1-9, wherein about 1.25 mM resorufin-beta-D-glucopyranoside is combined with the first cell lysate and/or the second cell lysate.
11. The method of any one of embodiments 1-10, wherein the first plurality of cells and the second plurality of cells are seeded in a multi-well plate.
12. The method of embodiment 11, wherein the first plurality of cells and/or the second plurality of cells are seeded at about 20,000 cells per well.
13. The method of any one of embodiments 1-12, wherein the test sample and/or the reference standard are serially diluted before transduction.
14. The method of any one of embodiments 1-13, wherein the first plurality of cells and the second plurality of cells are incubated from about 68 hours to about 81 hours before cell lysate harvesting.
15. The method of any one of embodiments 1-13, wherein the first plurality of cells and the second plurality of cells are incubated from about 66 hours to about 78 hours after transduction and before cell lysate harvesting.
16. The method of any one of embodiments 1-15, wherein the first plurality of cells is transduced by the test sample at at least two different multiplicities of infection (MOI) of the first recombinant virus.
17. The method of any one of embodiments 1-16, wherein the second plurality of cells is transduced by the reference standard at at least two different multiplicities of infection (MOI) of the second recombinant virus.
18. The method of any one of embodiments 1-17, wherein the first fluorescence reading and/or the second fluorescence reading reflect a measurement of GCase activity.
19. The method of embodiment 18, wherein the measurement of GCase activity is in relative fluorescence units (RFU)/hour.
20. The method of embodiment 19, wherein the comparing step (k) comprises performing a log transformation of the recombinant virus amount and RFU/hour and plotting a standard curve of the log of recombinant virus amount versus the log of RFU/hour for each of the test sample and the reference standard.
21. The method of embodiment 20, wherein the comparing step (k) comprises calculating a linear regression of the log of recombinant virus amount versus the log of RFU/hour for each of the test sample and the reference standard, thereby deriving a test sample slope and a reference standard slope.
22. The method of embodiment 21, wherein the comparing step (k) comprises calculating a linear regression with a common slope using the linear regressions obtained for each of the test sample and the reference standard.
23. The method of embodiment 22, wherein the relative potency is calculated using the formula: Relative potency (%)=$10\^((b-b_{reference})/A)\times100$.
24. The method of embodiment 22 or 23, wherein the ratio of the slope of the test sample to the common slope is from about 0.60 to about 1.40.
25. The method of any one of embodiments 22-24, wherein the ratio of the slope of the reference standard to the common slope is from about 0.60 to about 1.40.
26. The method of any one of embodiments 20-25, the method further comprising calculating an $R^2$ value for the linear regression of the test sample and the reference standard.
27. The method of embodiment 26, wherein the $R^2$ value for the test sample and the reference standard is greater than or equal to 0.9.

The invention claimed is:

1. A method for measuring the in vitro relative potency of a test sample comprising a first recombinant adeno-associated virus (rAAV) comprising a transgene encoding glucocerebrosidase (GCase), the method comprising:

a) transducing a first plurality of cells with the test sample;

b) incubating the transduced first plurality of cells under conditions sufficient to express GCase;

c) harvesting a first cell lysate from the transduced first plurality of cells;

d) combining the first cell lysate with resorufin-beta-D-glucopyranoside;

e) imaging the first cell lysate to obtain a first fluorescence reading reflecting a first measurement of GCase enzymatic activity;

f) transducing a second plurality of cells with a reference standard comprising a second rAAV comprising a transgene encoding GCase, wherein the reference standard has a known potency;

g) incubating the transduced second plurality of cells under conditions sufficient to express GCase;

h) harvesting a second cell lysate from the transduced second plurality of cells;

i) combining the second cell lysate with resorufin-beta-D-glucopyranoside;

j) imaging the second cell lysate to obtain a second fluorescence reading reflecting a second measurement of GCase enzymatic activity; and k) comparing the first fluorescence reading with the second fluorescence reading using parallel line analysis to calculate the in vitro relative potency of the test sample, wherein the in vitro relative potency is a measure of the transduction efficiency and transgene expression of the first rAAV relative to the second rAAV.

2. The method of claim 1, wherein the first rAAV and the second rAAV comprise identical transgenes encoding GCase.

3. The method of claim 1, wherein the first rAAV and the second rAAV independently comprise an AAV1, AAV2, AAV3, AAV4, AAV5, AAV6, AAV7, AAV8, AAV9, AAV10, or AAV11 capsid protein, or a variant of any of these capsid proteins.

4. The method of claim 3, wherein the first rAAV comprises an AAV9 capsid protein.

5. The method of claim 3, wherein the second rAAV comprises an AAV9 capsid protein.

6. The method of any one of claim 1, wherein the GCase comprises SEQ ID NO: 1.

7. The method of any one of claim 1, wherein the transgene encoding GCase comprises a codon-optimized nucleotide sequence.

8. The method of claim 7, wherein the codon-optimized nucleotide sequence comprises SEQ ID NO: 2.

9. The method of claim 1, wherein the first plurality of cells and the second plurality of cells are HEK-293T or HEK-293 cells.

10. The method of claim 1, wherein about 1.25mM resorufin-beta-D-glucopyranoside is combined with the first cell lysate and the second cell lysate.

11. The method of claim 1, wherein the first plurality of cells and the second plurality of cells are seeded in a multi-well plate.

12. The method of claim 11, wherein the first plurality of cells and the second plurality of cells are seeded at about 20,000 cells per well.

13. The method of claim 1, wherein the test sample and/or the reference standard are serially diluted before transduction.

14. The method of claim 1, wherein the first plurality of cells and the second plurality of cells are incubated from about 68 hours to about 81 hours before cell lysate harvesting.

15. The method of claim 1, wherein the first plurality of cells and the second plurality of cells are incubated from about 66 hours to about 78 hours after transduction and before cell lysate harvesting.

16. The method of claim 1, wherein the first plurality of cells is transduced by the test sample at at least two different multiplicities of infection (MOI) of the first recombinant virus.

17. The method of claim 1, wherein the second plurality of cells is transduced by the reference standard at at least two different multiplicities of infection (MOI) of the second recombinant virus.

18. The method of claim 1, wherein the measurement of GCase activity is in relative fluorescence units (RFU)/hour.

19. The method of claim 18, wherein the comparing step (k) comprises performing a log transformation of the recombinant virus amount and RFU/hour and plotting a standard curve of the log of recombinant virus amount versus the log of RFU/hour for each of the test sample and the reference standard.

20. The method of claim 19, wherein the comparing step (k) comprises calculating a linear regression of the log of recombinant virus amount versus the log of RFU/hour for each of the test sample and the reference standard, thereby deriving a test sample slope and a reference standard slope.

21. The method of claim 20, wherein the comparing step (k) comprises calculating a linear regression with a common slope using the linear regressions obtained for each of the test sample and the reference standard.

22. The method of claim 21, wherein the in vitro relative potency is calculated using the formula:

$$\text{Relative potency }(\%)=10\hat{}((b-b_{reference}=)/A)\times 100.$$

23. The method of claim 21, wherein the ratio of the slope of the test sample to the common slope is from about 0.60 to about 1.40.

24. The method of claim 21, wherein the ratio of the slope of the reference standard to the common slope is from about 0.60 to about 1.40.

25. The method of claim 19, the method further comprising calculating an $R^2$ value for the linear regression of the test sample and the reference standard.

26. The method of claim 25, wherein the $R^2$ value for the test sample and the reference standard is greater than or equal to 0.9.

* * * * *